United States Patent
Baichwal et al.

[11] Patent Number: 5,958,456
[45] Date of Patent: *Sep. 28, 1999

[54] CONTROLLED RELEASE FORMULATION (ALBUTEROL)

[75] Inventors: Anand Baichwal, Wappingers Falls, N.Y.; Troy W. McCall, New Milford, Conn.

[73] Assignee: Edward Mendell Co., Inc., Patterson, N.Y.

[ * ] Notice: This patent is subject to a terminal disclaimer.

[21] Appl. No.: 08/886,496

[22] Filed: Jul. 1, 1997

Related U.S. Application Data

[63] Continuation of application No. 08/553,008, Nov. 3, 1995, Pat. No. 5,662,933, which is a continuation-in-part of application No. 08/118,924, Sep. 9, 1993, Pat. No. 5,455,046.

[51] Int. Cl.$^6$ ....................................................... A61K 9/14
[52] U.S. Cl. ............................ 424/489; 424/488; 424/457; 424/468
[58] Field of Search ................................ 424/489, 488, 424/457, 468

[56] References Cited

U.S. PATENT DOCUMENTS

| | | | |
|---|---|---|---|
| 4,412,986 | 11/1983 | Kawata et al. | 424/80 |
| 4,562,069 | 12/1985 | Hegasy et al. | 424/80 |
| 4,673,564 | 6/1987 | Kawata et al. | 424/494 |
| 4,764,382 | 8/1988 | Kydonieus et al. | 424/449 |
| 4,765,990 | 8/1988 | Sugimoto et al. | 424/494 |
| 4,792,450 | 12/1988 | Kydonieus et al. | 424/449 |
| 4,792,452 | 12/1988 | Howard et al. | 424/475 |
| 4,808,413 | 2/1989 | Joshi et al. | 424/458 |
| 4,851,229 | 7/1989 | Magruder et al. | 424/457 |
| 4,867,985 | 9/1989 | Heafield et al. | 424/461 |
| 4,892,741 | 1/1990 | Ohm et al. | 424/479 |
| 4,904,699 | 2/1990 | Bauer | 514/972 |
| 4,940,587 | 7/1990 | Jenkins et al. | 424/480 |
| 4,942,040 | 7/1990 | Ragnarsson et al. | 424/486 |
| 4,973,469 | 11/1990 | Mulligan et al. | 424/461 |
| 4,994,276 | 2/1991 | Baichwal et al. | 424/440 |
| 5,007,790 | 4/1991 | Shell | 424/451 |
| 5,019,397 | 5/1991 | Wong et al. | 424/473 |
| 5,051,263 | 9/1991 | Barry et al. | 424/490 |
| 5,071,642 | 12/1991 | Lahr et al. | 424/474 |
| 5,128,143 | 7/1992 | Baichwal et al. | 424/464 |
| 5,132,116 | 7/1992 | Sournac et al. | 424/469 |
| 5,133,974 | 7/1992 | Paradissis et al. | 424/480 |
| 5,135,757 | 8/1992 | Baichwal et al. | 424/465 |
| 5,145,683 | 9/1992 | Rhodes | 424/451 |
| 5,169,638 | 12/1992 | Dennis et al. | 424/457 |
| 5,215,758 | 6/1993 | Krishnamurthy | 424/488 |
| 5,264,459 | 11/1993 | Chelmicka-Schorr et al. | 514/646 |
| 5,273,760 | 12/1993 | Oshlack et al. | 424/480 |
| 5,286,493 | 2/1994 | Oshlack et al. | 424/468 |
| 5,356,467 | 10/1994 | Oshlack et al. | 106/153 |
| 5,455,046 | 10/1995 | Baichwal | 424/457 |
| 5,662,933 | 9/1997 | Baichwal et al. | 424/457 |

FOREIGN PATENT DOCUMENTS

| | | |
|---|---|---|
| 1288049 | 8/1991 | Canada . |
| 0357793 | 3/1990 | European Pat. Off. . |
| 0232155 | 8/1997 | European Pat. Off. . |
| WO8902738 | 4/1989 | WIPO . |
| WO9206680 | 4/1992 | WIPO . |

*Primary Examiner*—Thurman K. Page
*Assistant Examiner*—William E. Benston, Jr.
*Attorney, Agent, or Firm*—Davidson,Davidson & Kappel,LLC

[57] ABSTRACT

A sustained release pharmaceutical formulation and methods of making and using the same are provided. The sustained release pharmaceutical formulation includes a sustained release excipient including a gelling agent, an inert pharmaceutical diluent, an optional hydrophobic material and/or hydrophobic coating, and a medicament for sustained oral administration.

16 Claims, 3 Drawing Sheets

CONTROLLED RELEASE FORMULATION (ALBUTEROL)

CROSS REFERENCE TO RELATED APPLICATIONS

This application is a continuation of U.S. Ser. No. 08/553,008, filed Nov. 3, 1995, now U.S. Pat. No. 5,662,933, which is a continuation-in-part of Ser. No. 08/118,924, filed Sep. 9, 1993, now U.S. Pat. No. 5,455,046.

FIELD OF THE INVENTION

The present invention relates to controlled release formulations which may be blended with a wide range of therapeutically active medicaments and made into controlled release solid dosage forms for oral administration.

BACKGROUND OF THE INVENTION

The advantages of controlled release products are well known in the pharmaceutical field and include the ability to maintain a desired blood level of a medicament over a comparatively longer period of time while increasing patient compliance by reducing the number administrations. These advantages have been attained by a wide variety of methods. For example, different hydrogels have been described for use in controlled release medicines, some of which are synthetic, but most of which are semi-synthetic or of natural origin. A few contain both synthetic and non-synthetic material. However, some of the systems require special process and production equipment, and in addition some of these systems are susceptible to variable drug release.

Oral controlled release delivery systems should ideally be adaptable so that release rates and profiles can be matched to physiological and chronotherapeutic requirements. In U.S. Pat. Nos. 4,994,276, 5,128,143, and 5,135,757, hereby incorporated by reference in their entireties, it is reported that a controlled release excipient which is comprised of a synergistic combination of heterodisperse polysaccharides (e.g., a heteropolysaccharide such as xanthan gum in combination with a polysaccharide gum capable of cross-linking with the heteropolysaccharide, such as locust bean gum, in an aqueous environment) is capable of being processed into oral solid dosage forms using either direct compression (i.e., dry granulation), following addition of drug and lubricant powder, conventional wet granulation, or a combination of the two. The release of the medicament from the formulations therein proceeded according to zero-order or first-order mechanisms.

The controlled release excipients disclosed in U.S. Pat. Nos. 4,994,276, 5,128,143, and 5,135,757 are commercially available under the trade name TIMERx® from Edward Mendell Co., Inc., Patterson, N.Y., which is the assignee of the present invention.

European Pat. No. 234670 B describes a controlled-release pharmaceutical formulation containing xanthan gum wherein the xanthan gum comprises from about 7.5 to about 28 percent, by weight, of the formulation except for a formulation wherein the controlled release carrier comprises a mixture of 15–50 parts by weight dimethylsiloxane, 30–100 parts by weight silicic acid, 30–100 parts by weight mannans or galactans or a mixture thereof, 50–150 parts by weight xanthans and 5–75 parts by weight micronized seaweed.

However, heretofore there has been no teaching of a controlled release formulation providing a novel and unexpected combination of suitable proportions of a homopolysaccharide such as, e.g., xanthan gum, a heteropolysaccharide, such as, e.g., locust bean gum, together with an inert diluent and a pharmacologically acceptable hydrophobic material, so as to provide an improvement in controlled release properties for such an active medicament.

OBJECTS AND SUMMARY OF THE INVENTION

It is therefore an object of the present invention to provide a controlled release formulation for a therapeutically active medicament.

It is a further object of the present invention to provide a method for preparing a controlled release formulation for a therapeutically active medicament.

It is yet another object of the present invention to provide a controlled release excipient which may be used in the preparation of a sustained release oral solid dosage form of a therapeutically active medicament that provides an even rate of release of an active medicament.

It is a further object of the present invention to provide a controlled release excipient which, when combined with an effective amount of a bronchodilator, such as albuterol, is suitable for providing a sustained release of that medicament so as to provide a therapeutically effective blood level of the medicament for e.g., 12 or 24 hours, without allowing an excessive early release of medication, and where the release kinetics are unaffected by the contents of the patient's gastrointestinal tract.

It is yet a further object of the present invention to provide a method for treating patients with an active medication in controlled release form.

The above-mentioned objects and others are achieved by virtue of the present invention, which relates in-part to a controlled release formulation comprising a therapeutically effective amount of a medicament, and a controlled release excipient comprising a gelling agent and a swelling agent, such as, for example, a homopolysaccharide, a heteropolysaccharide, an inert diluent.

In certain preferred embodiments of the invention, the ratio of the heteropolysaccharide gum to the homopolysaccharide gum is from about 1:3 to about 3:1. More preferably, the ratio is about 1:1. Preferably, the heteropolysaccharide gum includes xanthan gum and the homopolysaccharide gum includes locust bean gum.

The present invention is also related to a sustained release oral solid dosage form for albuterol or salts or derivatives thereof in an amount necessary to render a therapeutic effect in a human patient. The albuterol is present in an amount ranging from, e.g., about 2 through about 50% by weight of the total formulation, or preferably from about 1 through about 10% by weight or more preferably from about 1 through about 6% by weight of the total formulation.

The dosage form includes an inert pharmaceutical diluent so that the ratio of the inert diluent to the gelling agent is from about 1:8 to about 8:1. Preferably, the diluent is from the group consisting of a pharmaceutically acceptable saccharide, polyhydric alcohol, a pre-manufactured direct compression diluent, and mixtures of any of the foregoing. The diluent can also be a saccharide such as sucrose, dextrose, lactose, microcrystalline cellulose, fructose, xylitol, sorbitol, a starch, and mixtures thereof.

The dosage form optionally includes a pharmaceutically acceptable hydrophobic material. Any pharmaceutically acceptable hydrophobic material may be suitably employed.

Suitable hydrophobic materials include carboxymethylcellulose, cellulose acetate phthalate, polyvinyl acetate phthalate, hydroxypropyl-methylcellulose phthalate, ethylcellulose, a copolymer of acrylic and methacrylic and esters, waxes, shellac, zein, hydrogenated vegetable oils, and mixtures of any of the foregoing. Preferably, the hydrophobic material selected from cellulose ether, a cellulose ester and an alkylcellulose, such as ethylcellulose and carboxymethylcellulose. The hydrophobic material may be included in the dosage form in an amount effective to slow the hydration of the gelling agent when exposed to an environmental fluid.

The hydrophobic material is preferably present in an amount ranging from about 1 through about 90%, by weight, of the solid dosage form, and can also be present in an amount ranging from about 25% through about 50%, by weight, of the solid dosage form.

The medicament can be any medicament for which an orally administered controlled release form is desired. Preferably, the formulation is prepared to include a pharmaceutically effective amount of albuterol or a salt or derivative thereof.

The controlled release solid dosage form can be prepared in any conventional orally administered dosage form, including a tablet, as a granular form and as a granular form administered in a gelatin capsule containing a sufficient amount of the granules to provide an effective dose of the included therapeutically active medicament. For a tablet dosage form, at least part of a surface of the tablet can optionally be coated with a hydrophobic material to a weight gain from about 1 to about 20 percent, by weight. Further, a granular dosage form can optionally be coated with a hydrophobic coating material to a weight gain that ranges from about 1% to about 20%. The hydrophobic material can be selected from, e.g., a cellulose ether, a cellulose ester and an alkylcellulose. The hydrophobic material can optionally be applied before, during or after the process of tableting. In addition, if there is a need for an early release of the active medicament, the coating can optionally be formulated to include from about 10 to about 40 percent of the total amount of the active medicament in a quick release external layer.

The invention also relates to methods for preparing a controlled release solid dosage form as described above for providing an active medicament in an amount effective for treating a patient for from 12 to about 24 hours. The method includes the steps of preparing a sustained release excipient comprising from about 10 to about 99 percent by weight of a gelling agent comprising a heteropolysaccharide gum and a homopolysaccharide gum capable of cross-linking said heteropolysaccharide gum when exposed to an environmental fluid, the ratio of said heteropolysaccharide gum to said homopolysaccharide gum being from about 1:3 to about 3:1, and from about 0 to about 89 percent by weight of an inert pharmaceutical diluent, and optionally from about 1 to 90% by weight of a pharmaceutically acceptable hydrophobic material; and adding an effective amount of a medicament to provide a final product having a ratio of medicament to gelling agent from about 1:3 to about 1:8, so that a gel matrix is created.

The medicament to be added is preferably albuterol or salts or derivatives thereof in an amount ranging from, e.g., about 2 to about 50% by weight of the total formulation, or preferably from about 1 to about 10% by weight or more preferably from about 1 to about 6% by weight of the total formulation.

The resulting mixture of the sustained release excipient preferably includes from about 10 to about 75 percent gelling agent, from about 0 to about 90% hydrophobic material and from about 30 to about 75 percent inert diluent. Thereafter, the dosage form can be tableted, granulated with a pharmaceutically acceptable hydrophobic material or placed in gelatine capsules. Optionally the tablet can be coated with a hydrophobic coating to a weight gain from about 1% to about 20%.

Preferably, the medicament is albuterol or a salt or derivative thereof in an amount effective to provide therapeutically effective blood levels of said medicament for at least 24 hours.

The present invention is further related to a method of treating a patient comprising orally administering the sustained release albuterol tablets to a patient, thereby providing therapeutically effective blood levels of the medicament for at least about 24 hours.

By "sustained release" it is meant for purposes of the present invention that the therapeutically active medicament is released from the formulation at a controlled rate such that therapeutically beneficial blood levels (but below toxic levels) of the medicament are maintained over an extended period of time, e.g., providing a 24 hour dosage form.

The term "environmental fluid" is meant for purposes of the present invention to encompass, e.g., an aqueous solution, such as that used for in-vitro dissolution testing, or gastrointestinal fluid.

In one aspect the invention provides formulations having particular pharmacokinetic properties. Thus, simply by way of example, the invention provides formulations suitable for oral administration that, when orally administered to a patient, provide a medicament plasma concentration-time curve with an area under the curve-calculated to infinity ("$AUC_\infty$"), ranging from about 89 to about 150 (ng-hours/ml) or even from about 112 to about 129 (ng-hours/ml). Further, the formulations according to the invention can provide, e.g., an $AUC_\infty$ ranging from about 57 to about 157 (ng-hours/ml) (fasting patient) or from about 75 to about 162 (ng-hours/ml) (fed patient).

In addition, for example, mean peak plasma concentrations (Cmax) ranging from about 7 to about 12 ng/ml or even from about, 9.5 to about 12 ng/ml. are provided. Further, the formulations according to the invention can provide, e.g., a Cmax ranging from about 4.5 to about 19 ng/ml (fasting patient) or from about 6 to about 16 ng/ml (fed patient).

In another example, time to mean peak plasma concentration (Tmax) ranging from about 3 to about 10 hours or even from about 3.5 to about 8 hours are provided. Further, the formulations according to the invention can provide, e.g., a Tmax ranging from about 3 to about 6 hours (fasting patient) or from about 3 to about 8 hours (fed patient).

In a further example, the formulation according to the invention provides, for example, ratios of $AUC_\infty$ (fasting patient) to $AUC_\infty$ (fed patient) that range from about 0.50 to about 0.70.

Further still, the formulation provides, for example ranges of Cmax (fasting patient) divided by Cmax (fed patient) from about 0.90 to about 1.10.

DETAILED DESCRIPTION

As reported in U.S. Pat. Nos. 4,994,276, 5,128,143, and 5,135,757, the disclosures of which are hereby incorporated by reference herein in their entireties, the heterodisperse excipient comprises a gelling agent of both hetero- and homo-polysaccharides which exhibit synergism, e.g., the combination of two or more polysaccharide gums produce a higher viscosity and faster hydration than that which would be expected by either of the gums alone, the resultant gel being faster-forming and more rigid.

In the present invention, it has been found that a sustained release excipient comprising only the gelling agent (heterodisperse polysaccharides, e.g., xanthan gum and locust bean gum, may not be sufficient to provide a suitable sustained release of an active medicament to provide a 12 or 24 hour formulation, when the formulation is exposed to a fluid in an environment of use, e.g. an aqueous solution or gastrointestinal fluid.

In certain embodiments, the present invention is related to the surprising discovery that by granulating the sustained release excipient with a solution or dispersion of a pharmacologically acceptable hydrophobic material prior to admixture of the sustained release excipient with the medicament and tableting, the medicament may provide therapeutically effective blood levels for extended periods of time, e.g., from about 12 to about 24 hours. The hydrophobic material is present in a range from about 0 to about 90%, by weight, of the sustained release excipient and in a preferred embodiment, is present in a range from about 1 to 20 percent of the sustained release excipient or from about 25 to about 75 percent of the sustained release excipient.

The sustained release excipient can be granulated with a pharmacologically acceptable hydrophobic material such as, for, example, an alkylcellulose, a cellulose ether, a cellulose ester. In particular, the hydrophobic material can be alkylcellulose such as carboxymethylcellulose ("CMC"), cellulose acetate phthalate ("CAP"), hydroxypropylmethylcellulose phthalate ("HPMCP") or a polyvinyl acetate polymer such as polyvinyl acetate phthalate ("PVAP").

In certain preferred embodiments of the present invention, the sustained release excipient is prepared by mixing the gelling agent and an inert diluent. The gelling agent preferably ranges, e.g., from about 10 to about 75 percent of the sustained release excipient. Thereafter, the mixture is granulated with a solution or dispersion of a hydrophobic material in an amount effective to slow the hydration of the gelling agent without disrupting the hydrophilic matrix. Next, the medicament is added, and the resultant mixture is tableted.

In other preferred embodiments of the present invention, the tablets prepared as set forth above are then coated with a hydrophobic material to a weight gain from about 1 to about 20 percent by weight. The hydrophobic material can be an alkylcellulose such as, for example, an aqueous dispersion of ethylcellulose (commercially available, for example, as Aquacoat®, available from FMC or Surelease®, available from Colorcon).

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties.

An especially preferred heteropolysaccharide is xanthan gum, which is a high molecular weight (>$10^6$) heteropolysaccharide. Other preferred heteropolysaccharides include derivatives of xanthan gum, such as deacylated xanthan gum, the carboxymethyl ether, and the propylene glycol ester.

The homopolysaccharide gums used in the present invention which are capable of cross-linking with the heteropolysaccharide include the galactomannans, i.e., polysaccharides which are composed solely of mannose and galactose. Galactomannans which have higher proportions of unsubstituted mannose regions have been found to achieve more interaction with the heteropolysaccharide. Locust bean gum, which has a higher ratio of mannose to galactose, is especially preferred as compared to other galactomannans such as guar and hydroxypropyl guar.

The controlled release properties of the formulations of the present invention may be optimized when the ratio of heteropolysaccharide gum to homopolysaccharide material is about 1:1, although heteropolysaccharide gum in an amount of from about 20 to about 80 percent or more by weight of the heterodisperse polysaccharide material provides an acceptable slow release product. The combination of any homopolysaccharide gums known to produce a synergistic effect when exposed to aqueous solutions may be used in accordance with the present invention. It is also possible that the type of synergism which is present with regard to the gum combination of the present invention could also occur between two homogeneous or two heteropolysaccharides. Other acceptable gelling agents which may be used in the present invention include those gelling agents well-known in the art. Examples include vegetable gums such as alginates, carrageenan, pectin, guar gum, xanthan gum, modified starch, hydroxypropylmethylcellulose, methylcellulose, and other cellulosic materials such as sodium carboxymethylcellulose and hydroxypropylcellulose. This list is not meant to be exclusive.

The combination of xanthan gum with locust bean gum with or without the other homopolysaccharide gums is an especially preferred gelling agent. The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract.

The inert pharmaceutical diluent (i.e., filler) of the sustained release excipient preferably comprises a pharmaceutically acceptable saccharide, including a monosaccharide, a disaccharide, or a polyhydric alcohol, a pre-manufactured direct compression diluent, and/or mixtures of any of the foregoing. Examples of suitable inert pharmaceutical fillers include sucrose, dextrose, lactose, microcrystalline cellulose, fructose, xylitol, sorbitol, a starch, mixtures thereof and the like. However, it is preferred that a soluble pharmaceutical filler such as lactose, dextrose, sucrose, or mixtures thereof be used. If the mixture is to be manufactured without a wet granulation step, and the final product is to be tableted, it is preferred that all or part of the inert diluent comprise a pre-manufactured direct compression diluent. Such direct compression diluents are widely used in the pharmaceutical arts, and may be obtained from a wide variety of commercial sources. Examples of such pre-manufactured direct compression excipients include Emcocel® (microcrystalline cellulose, N.F.), Emdex® (dextrates, N.F.), and Tab-Fine® (a number of direct-compression sugars including sucrose, fructose, and dextrose), all of which are commercially available from Edward Mendell Co., Inc., Patterson, N.Y.). Other direct compression diluents include Anhydrous lactose (Lactose N.F., anhydrous direct tableting) from Sheffield Chemical, Union, N.J. 07083; Elcems® G-250 (Powdered cellulose, N.F.) from Degussa, D-600 Frankfurt (Main) Germany; Maltrin® (Agglomerated maltodextrin) from Grain Processing Corp., Muscatine, Iowa 52761; Neosorb 60® (Sorbitol, N.F., direct-compression) from Roquette Corp., 645 5th Ave., New York, N.Y. 10022; Nu-Tab® (Compressible sugar, N.F.) from Ingredient Technology, Inc., Pennsauken, N.J. 08110; Polyplasdone XL® (Crospovidone, N.F., cross-linked polyvinylpyrrolidone) from GAF Corp., New York, N.Y. 10020; Primojel® (Sodium starch glycolate, N.F., carboxymethyl starch) from Generichem Corp., Little Falls, N.J. 07424; Solka Floc® (Cellulose floc) from Edward Mendell Co., Carmel, N.Y. 10512; Fast-Flo Lactose® (Lactose N.F., spray dried) from Foremost Whey Products, Baraboo, Wis. 53913 and DMV Corp., Vehgel, Holland; and Sta-Rx 1500® (Starch 1500) (Pregelatinized starch, N.F., compressible) from Colorcon, Inc., West Point, Pa. 19486. However, it is preferred that a soluble pharmaceutical filler such as lactose, dextrose, sucrose, or mixtures thereof be used.

In certain embodiments of the present invention, the sustained release excipient comprises from about 10 to about 99 percent by weight of a gelling agent comprising a heteropolysaccharide gum and a homopolysaccharide gum and from about 0 to about 89 percent by weight of an inert pharmaceutical diluent. In other embodiments, the sustained release excipient comprises from about 10 to about 75 percent gelling agent, and from about 30 to about 75 percent inert diluent. In yet other embodiments, the sustained release excipient comprises from about 30 to about 75 percent gelling agent and from about 15 to about 65 percent inert diluent.

The sustained release excipient of the present invention may be further modified by incorporation of a hydrophobic material which slows the hydration of the gums without disrupting the hydrophilic matrix. This is accomplished in preferred embodiments of the present invention by granulating the sustained release excipient with the solution or dispersion of a hydrophobic material prior to the incorporation of the medicament. The hydrophobic material may be selected from an alkylcellulose such as ethylcellulose such as carboxymethyl-cellulose ("CMC"), other hydrophobic cellulosic materials, acrylic and/or methacrylic ester polymers, copolymers of acrylic and methacrylic esters, zein, waxes, other hydrophobic cellulosic materials, cellulose acetate phthalate ("CAP"), hydroxypropylmethylcellulose phthalate ("HPMCP") or a polyvinyl acetate polymer such as polyvinyl acetate phthalate ("PVAP"), hydrogenated vegetable oils, and any other pharmaceutically acceptable hydrophobic material known to those skilled in the art. The amount of hydrophobic material incorporated into the sustained release excipient is that which is effective to slow the hydration of the gums without disrupting the hydrophilic matrix formed upon exposure to an environmental fluid.

In certain preferred embodiments of the present invention, the hydrophobic material is included in the sustained release excipient in an amount from about 1 to about 20 percent by weight. The solvent for the hydrophobic material may be an aqueous or organic solvent, or mixtures thereof.

Examples of commercially available alkylcelluloses are Aquacoat® (aqueous dispersion of ethylcellulose available from FMC), Surelease® (aqueous dispersion of ethylcellulose available from Colorcon). Examples of commercially available acrylic polymers suitable for use as the hydrophobic material include Eudragit® RS and RL (copolymers of acrylic and methacrylic acid esters having a low content (e.g, 1:20 or 1:40) of quaternary ammonium compounds).

Once the sustained release excipient of the present invention has been prepared, it is then possible to blend the same with the medicament, e.g., in a high shear mixer. In one embodiment, the formulation is prepared by dry blending the components, e.g., a heteropolysaccharide, a homopolysaccharide, an inert filler, and a hydrophobic material, optionally followed by the addition of a suitable amount of water, with continued blending, followed by dry granulation in a fluid bed dryer and then milling of the resulting granulation product.

A wide variety of therapeutically active agents can be used in conjunction with the present invention. The therapeutically active agents (e.g., pharmaceutical agents) which may be used in the compositions of the present invention include drugs ranging in solubility from water soluble to water insoluble. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrazepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

In a preferred embodiment, the therapeutically active agents are sympathomimetics such as, dobutamine hydrochloride, dopamine hydrochloride, ephedrine sulfate, epinephrine, fenfluramine hydrochloride, isoetharine, isoproterenol, mephentermine sulfate, metaproterenol sulfate, metaraminol bitartrate, methoxamine hydrochloride, norepinephrine bitartrate, phenylephrine hydrochloride, phenylpropanolamine hydrochloride, pseudoephedrine, ritodrine hydrochloride, terbutaline sulfate, tetrahydrozoline hydrochloride, triprolidine and pseudoephedrine, xylometazoline hydrochloride, isoproterenol and dobutamine as well as beta2 selective adrenergic agonists, including, for example, terbutaline, albuterol, isoetharine, pirbuterol and bitolterol (GOODMAN AND GILMAN's, THE PHARMACOLOGICAL BASIS OF THERAPEUTICS, Eighth Edition, the disclosure of which is incorporated herein by reference in its entirety).

Generally any flavoring or food additive such as those described in *Chemicals Used in Food Processing*, pub 1274 by the National Academy of Sciences, pages 63–258, incorporated herein in its entirety, may be used. Generally, the final product may include from about 0.1% to about 5% by weight flavorant.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857–884, hereby incorporated by reference in its entirety), stabilizers, binders, odor controlling agents, and preservatives.

Alternatively, the inventive formulation can be utilized in other applications wherein it is not compressed. For example, the granulate can be admixed with an active ingredient and the mixture then filled into capsules. The granulate can further be molded into shapes other than those typically associated with tablets. For example, the granulate together with active ingredient can be molded to "fit" into a particular area in an environment of use (e.g., an implant). All such uses would be contemplated by those skilled in the art and are deemed to be encompassed within the scope of the appended claims.

A hydrophobic material (e.g., a hydrophobic polymer) may be dissolved in an organic solvent or dispersed in an aqueous solution. Thereafter, the hydrophobic material may be used to coat the granulate of medicament/sustained release excipient. The granulate may be coated with the hydrophobic coating to a weight gain of, e.g., from about 1 to about 20 percent, and preferably from about 5 to about 10 percent. The granulation is then preferably dried. Thereafter, the granulate may be further formulated into an appropriate oral dosage form, for example, by compression of the resulting granulate into appropriately sized tablets, by filling gelatin capsules with an appropriate amount of the granulate (with or without compression of the granulate), as well as use in the manufacture of other oral dosage forms known to those skilled in the art. This embodiment may be particularly beneficial to reduce the amount of drug released during the initial phases of dissolution when the formulation is exposed to fluid in an environment of use, e.g., in vitro dissolution or in the gastrointestinal tract.

An effective amount of any generally accepted pharmaceutical lubricant, including the calcium or magnesium soaps may be added to the above-mentioned ingredients of the excipient be added at the time the medicament is added, or in any event prior to compression into a said dosage form. An example of a suitable lubricant is magnesium stearate in an amount of about 0.5 to about 3% by weight of the solid dosage form. An especially preferred lubricant is sodium stearyl fumarate, NF, commercially available under the trade name Pruv® from the Edward Mendell Co., Inc.

The sustained release excipients of the present invention have uniform packing characteristics over a range of different particle size distributions and are capable of processing into the final dosage form (e.g., tablets) using either direct compression, following addition of drug and lubricant powder, or conventional wet granulation.

The properties and characteristics of a specific excipient system prepared according to the present invention is dependent in part on the individual characteristics of the homo and hetero polysaccharide constituents, in terms of polymer solubility, glass transition temperatures etc., as well as on the synergism both between different homo- and heteropolysaccharides and between the homo and heteropolysaccharides and the inert saccharide constituent(s) in modifying dissolution fluid-excipient interactions.

The combination of the gelling agent (i.e., a mixture of xanthan gum and locust beam gum) with the inert diluent provides a ready-to-use product in which a formulator need only blend the desired active medicament and an optional lubricant with the excipient and then compress the mixture to form slow release tablets. The excipient may comprise a physical admix of the gums along with a soluble excipient such as compressible sucrose, lactose or dextrose, although it is preferred to granulate or agglomerate the gums with plain (i.e., crystalline) sucrose, lactose, dextrose, etc., to form an excipient. The granulate form has certain advantages including the fact that it can be optimized for flow and compressibility; it can be tableted, formulated in a capsule, extruded and spheronized with an active medicament to form pellets, etc.

The pharmaceutical excipients prepared in accordance with the present invention may be prepared according to any agglomeration technique to yield an acceptable excipient product. In dry granulation techniques, the excipients, i.e., the desired amounts of the heteropolysaccharide gum, the homopolysaccharide gum, and the inert diluent are mixed with an active medicament and the mixture is then formed into tablets and the like by compression, without the addition of water or other solvent.

In wet granulation techniques, the desired amounts of the heteropolysaccharide gum, the homopolysaccharide gum, and the inert diluent are mixed together and thereafter a moistening agent such as water, propylene glycol, glycerol, alcohol or the like is added to prepare a moistened mass. Next, the moistened mass is dried. The dried mass is then milled with conventional equipment into granules. Therefore, the excipient product is ready to use.

The sustained release excipient is free-flowing and directly compressible. Accordingly, the excipient may be mixed in the desired proportion with a therapeutically active medicament and optional lubricant (dry granulation). Alternatively, all or part of the excipient may be subjected to a wet granulation with the active ingredient and thereafter tableted. When the final product to be manufactured is tablets, the complete mixture, in an amount sufficient to make a uniform batch of tablets, is then subjected to tableting in a conventional production scale tableting machine at normal compression pressure, i.e. about 2000–1600 lbs/sq in. However, the mixture should not be compressed to such a degree that there is subsequent difficulty in its hydration when exposed to gastric fluid.

One of the limitations of direct compression as a method of tablet manufacture is the size of the tablet. If the amount of active (drug) is high, a pharmaceutical formulator may choose to wet granulate the active medicament with other excipients to attain a more compact tablet. Usually the amount of filler/binder or excipients needed in wet granulation is less than that in direct compression since the process of wet granulation contributes to some extent toward the desired physical properties of a tablet.

The average tablet size for round tablets is preferably about 300 mg to 750 mg and for capsule-shaped tablets about 750 mg to 1000 mg.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec. Tablets compacted using an instrumented rotary tablet machine have been found to possess strength profiles which are largely independent of the inert saccharide component. Scanning electron photomicrographs of largely tablet surfaces have provided qualitative evidence of extensive plastic deformation on compaction, both at the tablet surface and across the fracture surface, and also show evidence of surface pores through which initial solvent ingress and solution egress may occur.

In certain embodiments of the invention, the tablet is coated with a sufficient amount of a hydrophobic material, such as, e.g., a hydrophobic polymer, to render the formulation capable of providing a release of the medicament such that a 12 or 24 hour formulation is obtained. The hydrophobic material included in the tablet coating may be the same or different material as compared to the hydrophobic material which is optionally granulated with the sustained release excipient.

In other embodiments of the present invention, the tablet coating may comprise an enteric coating material in addition to or instead or the hydrophobic coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L 100–555.

In further embodiments, the dosage form may be a coating with a hydrophilic coating in addition to or instead of the above-mentioned coatings. An example of a suitable material which may be used for such a hydrophilic coating is hydroxypropylmethylcellulose (e.g., Opadry®, commercially available from Colorcon, West Point, Pa.).

The coatings may be applied in any pharmaceutically acceptable manner known to those skilled in the art. For example, in one embodiment, the coating is applied via a fluidized bed or in a coating pan. For example, the coated tablets may be dried, e.g., at about 60–70° C. for about 3–4 hours in a coating pan. The solvent for the hydrophobic material or enteric coating may be organic, aqueous, or a mixture of an organic and an aqueous solvent. The organic solvents may be, e.g., isopropyl alcohol, ethanol, and the like, with or without water.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference herein in its entirety. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the hydrophobic materials.

The support platform may have a thickness of, e.g., about 2 mm if applied by compression, and about 10 $\mu$ if applied via spray-coating or immersion-coating. Generally, in embodiments of the invention wherein a hydrophobic material or enteric coating is applied to the tablets, the tablets are coated to a weight gain from about 1 to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In certain embodiments of the present invention, the tablet core includes an additional dose of the medicament included in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of a therapeutically active agent is needed to provide therapeutically effective blood levels of the active agent when the formulation is first exposed to gastric fluid. The loading dose of medicament included in the coating layer may be, e.g., from about 10% to about 40% of the total amount of medicament included in the formulation.

Albuterol Controlled Release Formulation

In a more preferred embodiment, the therapeutically active agent is albuterol, or salts or derivatives thereof (e.g., albuterol sulfate). Albuterol sulfate is a beta2-selective adrenergic agonist and is indicated for the relief of bronchospasm in patients with reversible obstructive airway disease. Patient compliance and evenly maintained blood levels of the active drug are important for achieving good control of the symptoms of bronchospasm in such patients. The half-life of albuterol sulfate in the human body is only about 5 hours. Thus, a controlled release form for the sustained delivery of albuterol provides improved patient compliance by reducing the number of doses per day and also provides more consistent blood levels of albuterol for patients in need of such treatment.

The albuterol controlled release formulation is composed of synergistic heterodisperse polysaccharides together with a saccharide component. The synergism between the homo- and hetero-polysaccharide components enables the manipulation of different rate controlling mechanisms. In order to achieve appropriate drug release, the saccharides were optimized based upon the magnitude of interactions and the ratio of one saccharide to another.

Preparation

The albuterol containing formulation according to the invention is prepared, for example, by dry blending the components, e.g., a heteropolysaccharide, a homopolysaccharide, an inert filler, and a hydrophobic material, followed by the addition of a suitable amount of water, with continued blending, followed by dry granulation in a fluid bed dryer and then milling of the resulting granulation product. Albuterol sulfate, in an amount ranging from, e.g., about 2 through about 50% by weight of the total formulation, or preferably from about 1 through about 10% by weight or more preferably from about 1 through about 6% by weight of the total formulation, is then compounded with the granulation product and formed into pills, caplets or capsules. Whatever the formulation, it is preferred that such pills, caplets or capsules each contain an effective therapeutic amount of albuterol or a derivative or salt thereof. Simply by way of example, the pills, caplets or capsules can contain an amount of albuterol sulfate equivalent to about 4 to about 16 mg of albuterol free base per dosage unit of the free base. More preferably, the pills, caplets or capsules can contain an amount of albuterol sulfate equivalent to about 8 to about 12 mg of the free base. Simply by way of comparison, 9.6 mg of albuterol sulfate is equivalent to 8 mg of free base. Effective amounts of other pharmaceutically acceptable albuterol derivatives or salts thereof may be used, with the amounts adjusted in proportion to the weight ranges provided for albuterol free base.

Dissolution Testing

The test formulations were evaluated under a variety of dissolution conditions to determine the effects of pH, media, agitation and apparatus. Dissolution tests were performed using a USP Type III (VanKel Bio-Dis II) apparatus. Effects of pH, agitation, polarity, enzymes and bile salts were evaluated.

Bioavailability Study

A study was conducted to evaluate the bioavailability of a test formulation of albuterol sulfate using a randomized, balanced, open label, single dose, crossover design. The study was performed using 12 healthy male and female volunteers between the ages of 18 and 35. Blood samples were removed at 0, 0.5, 1, 2, 3, 4, 6, 8, 10, 12, 15 and 25 hours. Except for the "fed" treatment in which the subjects received a standard high fat breakfast, no food was allowed until a standard lunch was served four hours after the dose was administered. The data from each time point were used to derive pharmacokinetic parameters: area under plasma concentration-time curve ("AUC") such as AUC0-t, AUC0-∞, mean peak plasma concentration ("Cmax") and time$_A$ to mean peak plasma concentration ("Tmax") which data confirmed that the formulation according to the invention provided controlled release of albuterol sulfate.

The invention is further described in the following examples, based upon the above described methods, which are in no way intended to limit the scope of the invention.

EXAMPLES 1–2

Preparation of Controlled Release Formulations with Carboxymethylcellulose and Dissolution Tests Thereon The sustained release excipient was prepared by dry blending the requisite amounts of xanthan gum, locust bean gum, a pharmaceutically acceptable hydrophobic polymer and an inert diluent in a high-speed mixer/granulator for 2 minutes. While running choppers/impellers, the water was added and the mixture was granulated for another 2 minutes. The granulation was then dried in a fluid bed dryer to a loss on drying weight ("LOD") of between 4 and 7%. The granulation was then milled using 20 mesh screens. The ingredients of the sustained release excipients used for Examples 1–2 are set forth in Table 1 below:

TABLE 1

The hydrophobic polymer is carboxymethylcellulose ("CMC").

| | Component | Example 1 | Example 2 |
|---|---|---|---|
| 1. | Xanthan gum | 10% | 10% |
| 2. | Locust bean gum | 10 | 10 |

TABLE 1-continued

The hydrophobic polymer is carboxymethylcellulose ("CMC").

| | Component | Example 1 | Example 2 |
|---|---|---|---|
| 3. | CMC | 10 | 30 |
| 4. | Dextrose | 70 | 50 |
| 5. | Water | 23* | 23* |

*Removed during processing.

Next, the sustained release excipient prepared as detailed above is dry blended with a desired amount of medicament (in the following examples the medicament is albuterol sulfate), in a V-blender for 10 minutes. A suitable amount of tableting lubricant Pruv® (sodium stearyl fumarate, NF, commercially available from the Edward Mendell Co., Inc.) for the following examples is added and the mixture is blended for another 5 minutes. This final mixture is compressed into tablets, each tablet containing 2.9% (Ex. 1) or 4.7% (Ex. 2) by weight, respectively, of albuterol sulfate. The tablets produced by Examples 1 and 2 weighed 334.6 mg and 204.7 mg, respectively. The proportions of the tablets of Examples 1 and 2 are set forth in Table 2 below.

TABLE 2

| | Component | Example 1 | Example 2 |
|---|---|---|---|
| 1. | SRE* | 95.6% | 93.8% |
| 2. | Albuterol sulfate | 2.9 | 4.7 |
| 3. | Sodium stearyl fumarate | 1.5 | 1.5 |

*Sustained release excipient.

Dissolution tests were then carried out on the tablets of Examples 1 and 2. The dissolution tests were conducted in an automated USP dissolution apparatus (Paddle Type II, pH 7.5 buffer, 50 rpm in 500 mL.) The results are set forth as percent release as a function of time, in hours.

TABLE 3

| | Example 1 | Example 2 |
|---|---|---|
| Time (hrs) | | |
| 0 (% release) | 0.0 | 0.0 |
| 2 | 28.2 | 30.7 |
| 4 | 41.5 | 49.5 |
| 6 | 54.5 | 67.2 |
| 8 | 64.3 | 79.8 |
| 10 | 71.0 | 91.2 |
| 12 | 78.7 | 96.5 |
| Tablet wt (mg) | 334.6 | 204.7 |
| Diameter (in) | ⅜ | ⅜ |
| Hardness (Kp) | 6.5 | 2.6 |

The tablet of Example 1, with a higher percentage of sustained release excipient, provided the most prolonged release in the dissolution test.

EXAMPLES 3–4

Preparation of Controlled Release Formulations with Cellulose Acetate Phthalate and Dissolution Tests Thereon The sustained release excipient was prepared by dry blending the requisite amounts of xanthan gum, locust bean gum, a pharmaceutically acceptable hydrophobic polymer and an inert diluent as described for Examples 1–2, supra, but with cellulose acetate phthalate ("CAP") as the hydrophobic polymer, as detailed by Table 4, below, for Examples 3 and 4.

TABLE 4

| | Component | Example 3 | Example 4 |
|---|---|---|---|
| 1. | Xanthan gum | 15% | 15% |
| 2. | Locust bean gum | 15 | 15 |
| 3. | CAP | 10 | 30 |
| 4. | Dextrose | 60 | 40 |
| 5. | Water | 10* | 17* |

*Removed during processing.

Next, the sustained release excipient prepared as detailed above was dry blended with a desired amount of albuterol sulfate, as described for Examples 1–2, supra. This final mixture was then compressed into tablets, each tablet containing 2.9% by weight of albuterol sulfate. The tablets produced by Examples 3 and 4 weighed 334.6 mg. The proportions of the tablets of Examples 3 and 4 are set forth in Table 5 below:

TABLE 5

| | Component | Example 3 | Examples 4 |
|---|---|---|---|
| 1. | SRE* | 95.6% | 95.6% |
| 2. | Albuterol sulfate | 2.9 | 2.9 |
| 3. | Sodium stearyl fumarate | 1.5 | 1.5 |

*Sustained release excipient.

Dissolution tests were then carried out on the tablets of Examples 3 and 4. The dissolution tests were conducted in an automated USP dissolution apparatus in such a way as to model passage through the gastrointestinal tract, in the stomach (acid buffer with a pH of 1.5 for time: 0 though 1 hour) and in the intestines (alkaline buffer with a pH of 7.5 for time: 1 through 12 hours) (Paddle Type II, 50 rpm in 500 mL.) The results are set forth as percent release as a function of time, in hours, in Table 6 below.

TABLE 6

| | Example 3 | Example 4 |
|---|---|---|
| Time (hrs) | | |
| 0 (% release) | 0.0 | 0.0 |
| 1 | 36.0 | 36.2 |
| 2 | 50.2 | 49.4 |
| 4 | 65.1 | 61.4 |
| 6 | 73.5 | 70.7 |
| 8 | 83.1 | 77.0 |
| 10 | 86.3 | 81.6 |
| 12 | 91.0 | 86.1 |
| Tablet wt (mg) | 334.6 | 334.6 |
| Diameter (in) | 3/8 | 3/8 |
| Hardness (Kp) | 5.8 | 5.8 |

The tablet tested in Example 4 provided the most prolonged release in the dissolution test.

EXAMPLES 5–6

Preparation of Controlled Release Formulations with Polyvinyl Acetate Phthalate and Dissolution Tests Thereon The sustained release excipient was prepared by dry blending the requisite amounts of xanthan gum, locust bean gum, a pharmaceutically acceptable hydrophobic polymer and an inert diluent as described for Examples 1–2, supra, but with polyvinyl acetate phthalate ("PVAP") as the hydrophobic polymer, as detailed by Table 7, below, for Examples 5 and 6.

TABLE 7

| | Component | Example 5 | Example 6 |
|---|---|---|---|
| 1. | Xanthan gum | 15% | 15% |
| 2. | Locust bean gum | 15 | 15 |
| 3. | PVAP | 10 | 30 |
| 4. | Dextrose | 60 | 40 |
| 5. | Water | 18* | 23* |

*Removed during processing.

Next, the sustained release excipient prepared as detailed above was dry blended with a desired amount of albuterol sulfate, as described for Examples 1–2, supra. This final mixture was then compressed into tablets, each tablet containing 2.9% by weight of albuterol sulfate. The tablets produced by Examples 5 and 6 weighed 334.6 mg, respectively. The proportions of the tablets of Examples 5 and 6 are set forth in Table 8 below:

TABLE 8

| | Component | Example 5 | Example 6 |
|---|---|---|---|
| 1. | SRE* | 95.6% | 95.6% |
| 2. | Albuterol sulfate | 2.9 | 2.9 |
| 3. | Sodium stearyl fumarate | 1.5 | 1.5 |

*Sustained release excipient.

Dissolution tests were then carried out on the tablets of Examples 5 and 6. The dissolution tests were conducted in an automated USP dissolution apparatus in such a way as to model passage through the gastrointestinal tract, in the stomach (acid buffer with a pH of 1.5 for time: 0 though 1 hour) and in the intestines (alkaline buffer with a pH of 7.5 for time: 1 through 12 hours) (Paddle Type II, 50 rpm in 500 mL.) The results are set forth as percent release as a function of time, in hours, in Table 9 below.

TABLE 9

| | Example 5 | Example 6 |
|---|---|---|
| Time (hrs) | | |
| 0 (% release) | 0.0 | 0.0 |
| 1 | 36.4 | 36.5 |
| 2 | 51.3 | 47.4 |
| 4 | 66.2 | 57.6 |
| 6 | 71.8 | 66.0 |
| 8 | 79.9 | 70.4 |
| 10 | 84.2 | 77.2 |
| 12 | 86.4 | 77.7 |
| Tablet wt (mg) | 334.6 | 334.6 |
| Diameter (in) | 3/8 | 3/8 |
| Hardness (Kp) | 5.9 | 8.6 |

The tablet tested in Example 6 provided the most prolonged release in the dissolution test.

EXAMPLES 7–8

Preparation of Controlled Release Formulations with Hydroxypropylmethylcellulose Phthalate and Dissolution Tests Thereon The sustained release excipient was prepared by dry blending the requisite amounts of xanthan gum, locust bean gum, a pharmaceutically acceptable hydrophobic polymer and an inert diluent as described for Examples 1–2, supra, but with hydroxypropylmethylcellulose phthalate ("HPMCP") as the hydrophobic polymer, as detailed by Table 10, below, for Examples 7 and 8.

TABLE 10

| | Component | Example 7 | Example 8 |
|---|---|---|---|
| 1. | Xanthan gum | 15% | 15% |
| 2. | Locust bean gum | 15 | 15 |
| 3. | HPMCP | 10 | 30 |
| 4. | Dextrose | 60 | 40 |
| 5. | Water | 13* | 18* |

*Removed during processing.

As for the previous examples, the sustained release excipient was prepared as detailed above and then dry blended with a desired amount of albuterol sulfate, as described for Examples 1–2, supra. This final mixture was then compressed into tablets, each tablet containing 2.9% by weight of albuterol sulfate. The tablets produced by Examples 7 and 8 weighed 334.6 mg, respectively. The proportions of the tablets of Examples 7 and 8 are set forth in Table 11 below:

TABLE 11

| | Component | Example 7 | Example 8 |
|---|---|---|---|
| 1. | SRE* | 95.6% | 95.6% |
| 2. | Albuterol sulfate | 2.9 | 2.9 |
| 3. | Sodium stearyl fumarate | 1.5 | 1.5 |

*Sustained release excipient.

The dissolution tests were conducted in an automated USP dissolution apparatus in such a way as to model passage through the gastrointestinal tract, as described supra for, e.g., Examples 5–6. The results are set forth as percent release as a function of time, in hours, in Table 12 below.

TABLE 12

| | Example 7 | Example 8 |
|---|---|---|
| Time (hrs) | | |
| 0 (% release) | 0.0 | 0.0 |
| 1 | 33.7 | 32.7 |
| 2 | 48.2 | 42.8 |
| 4 | 63.9 | 60.3 |
| 6 | 74.8 | 71.2 |
| 8 | 79.6 | 74.6 |
| 10 | 85.6 | 82.3 |
| 12 | 87.0 | 87.2 |
| Tablet wt (mg) | 334.6 | 334.6 |
| Diameter (in) | 3/8 | 3/8 |
| Hardness (Kp) | 6.5 | 8.3 |

The data of Table 12 indicates that both Examples 7 and 8 provided effective prolongation of albuterol release in the dissolution test.

EXAMPLES 9–12

Preparation of Controlled Release Formulations with Ethylcellulose Coating and Dissolution Tests Thereon The sustained release excipient was prepared by dry blending the requisite amounts of xanthan gum, locust bean gum and an inert diluent as described for Examples 1–2, supra, but with no hydrophobic polymer, and with an extra 2 minutes of granulation after the addition of the components (for 4 total minutes of post-addition granulation). Ethylcellulose aqueous dispersion was substituted for water in the above methods. The components of the excipient for Examples 9–12 are detailed by Table 13, below.

TABLE 13

| | Component | Excipient for Examples 9–12 |
|---|---|---|
| 1. | Xanthan gum | 12% |
| 2. | Locust bean gum | 18 |
| 3. | Dextrose | 65 |
| 4. | EAD* | 5* |

*EAD is an ethylcellulose aqueous dispersion containing approximately 25% by weight of solids. The amount added to the formulation (i.e., 5%) is solids only. Available commercially as, e.g., Surelease ®, from Colorcon.

The xanthan gum and locust bean gum was dry blended in a V-blender for 10 minutes, the dextrose was added and the mixture blended for another 5 minutes. The EAD was then added, followed by an additional 5 minutes of blending. The resulting granulation was then compressed into tablets with sodium stearyl fumarate, as a tableting lubricant. The tablets were then coated with additional ethylcellulose aqueous dispersion. To accomplish this, ethylcellulose (Surelease®, 400 g) was mixed with water (100 g) to form an aqueous suspension. Thereafter, the tablets were coated in a Keith Machinery coating pan (diameter 350 mm; pan speed 20 rpm; spray-gun nozzle 0.8 mm; tablets bed temperature 40°–50° C.; charge per batch 1 kg; dry air—Conair Prostyle 1250, 60°–70° C.). The tablets were coated to a weight gain of about 5%.

The tablets weighed 181.4 mg, respectively. The proportions of the tablets are set forth in Table 14 below:

TABLE 14

| | Component | Percent |
|---|---|---|
| 1. | SRE* | 8.2% |
| 2. | Albuterol sulfate | 5.3 |
| 3. | Polyvinyl acetate phthalate | 5.0 |
| 4. | Sodium stearyl fumarate | 1.5 |

*Sustained release excipient.

The dissolution tests were conducted in an automated USP dissolution apparatus in such a way as to model passage through the gastrointestinal tract, as described supra for, e.g., Examples 5–6. The results are set forth as percent release as a function of time, in hours, in Table 15, below. The columns are identified as "Uncoated" (Ex. 9) 2% (Ex. 10), 3% (Ex. 11) and 4% (Ex. 12) coating by weight.

TABLE 15

| Time (hrs) | Ex. 9 Uncoated | Ex. 10 2% | Ex. 11 3% | Ex. 12 4% (coat % w/w) |
|---|---|---|---|---|
| 0 (% release) | 0.0 | 0.0 | 0.0 | 0.0 |
| 1 | 41.7 | 11.2 | 0.0 | 0.0 |
| 2 | 56.7 | 21.9 | 2.3 | 0.0 |
| 4 | 73.0 | 41.2 | 16.2 | 4.6 |
| 6 | 82.5 | 60.3 | 37.1 | 21.3 |
| 8 | 87.9 | 74.9 | 54.5 | 40.3 |
| 10 | 91.0 | 82.5 | 65.2 | 54.0 |
| 12 | 93.9 | 88.5 | 84.1 | 67.5 |

Tablet wt (mg) 181.4
Diameter (in) 3/8
Hardness (Kp) 7.9

The above table clearly indicates that a prolongation of release is obtained that is proportional to the percent of hydrophobic coating, by weight.

In order to determine the differences, if any, in dissolution kinetics between a fed state and a fasting state for the series of coated tablets as tested above in Examples 9–12, the same tablets were tested, in vitro, for dissolution rates in a solution containing 30% peanut oil ("fed") to model a gastrointestinal tract with a typical dietary fat load. The control determined the dissolution rates in a solution lacking the fat load ("fasted"). The pH—time protocol (ranging from acid to alkaline to model digestive processes) is set forth below in Table 16, below.

TABLE 16

Fed/Fast Dissolution Protocol

|  | "Fasted" | "Fed" |
|---|---|---|
| Apparatus: | Type III | Type III |
| Media: | 0–1 hr pH 1.5 | 30% peanut oil |
|  | 1–2 hr pH 3.5 |  |
|  | 2–4 hr pH 5.5 |  |
|  | 4–12 hr pH 7.5 |  |
| Agitation: | 15 cpm | 15 cpm |
| Volume: | 250 mL | 250 mL |

TABLE 17

Fed/Fast Dissolution Results

| Time (hrs) | "Fasted" Uncoated | "Fasted" 2% | "Fed" Uncoated | "Fed" 2% |
|---|---|---|---|---|
| 0 (% release) | 0.0 | 0.0 | 0.0 | 0.0 |
| 1 | 48.8 | 15.5 | 28.8 | 18.4 |
| 2 | 68.5 | 28.8 | 49.8 | 39.9 |
| 4 | 87.2 | 49.5 | 91.9 | 78.9 |
| 6 | 96.1 | 65.9 | 100.0 | 97.3 |
| 8 | 100.0 | 80.7 | 100.0 | 100.0 |
| 12 | 100.0 | 100.0 | 100.0 | 100.0 |

As can be appreciated from table 17, the dissolution rates (in vitro) in the presence of 30% peanut oil ("Fed") are not significantly different from the dissolution rates in the absence of the 30% peanut oil ("Fast"), thus demonstrating both the improved control of release rate provided by the 2% ethylcellulose coating and the freedom from significant "Fed/Fast" effects provided by the formulations of the present invention.

Results and Discussion

Figure 1:
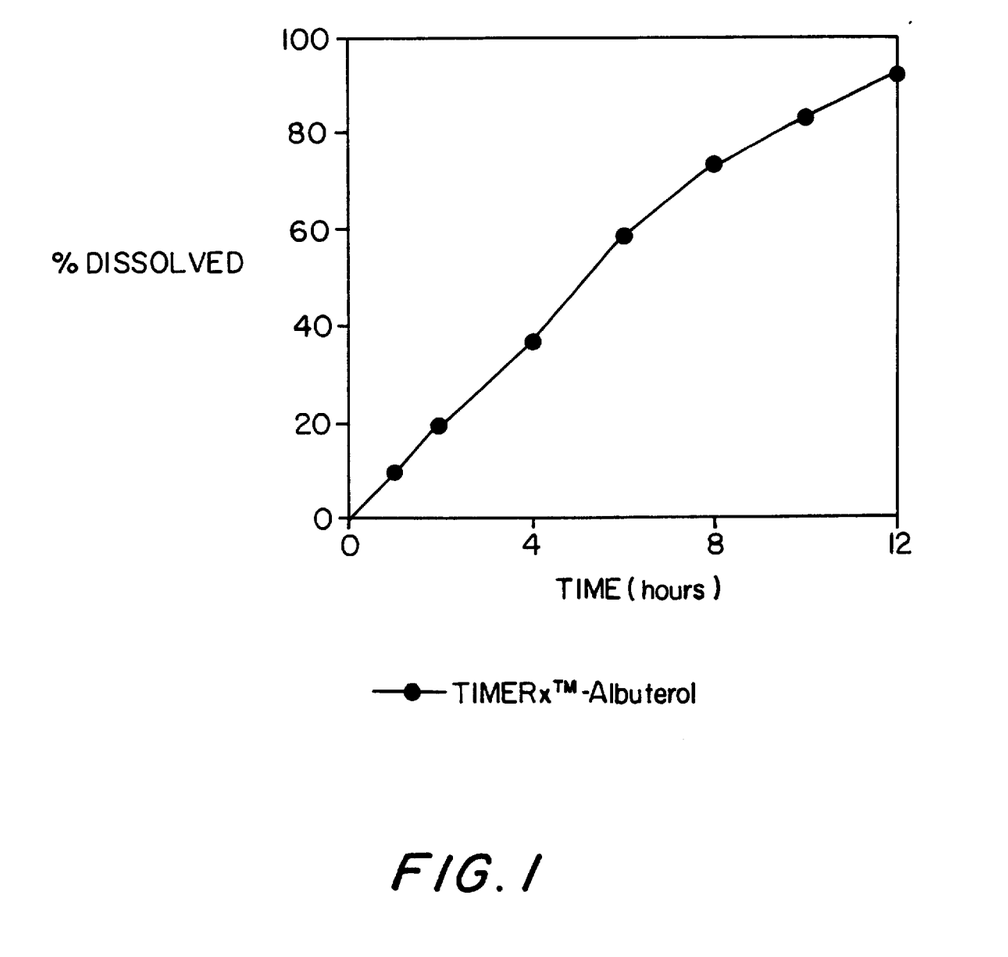
FIG. 1 shows a dissolution profile of an albuterol containing tablet formulated according to Table 14 and Table 15 (Example 10) and conducted as a Type II dissolution with a pH change to simulate gastric passage and stirring at 50 rpm.
Figure 2:
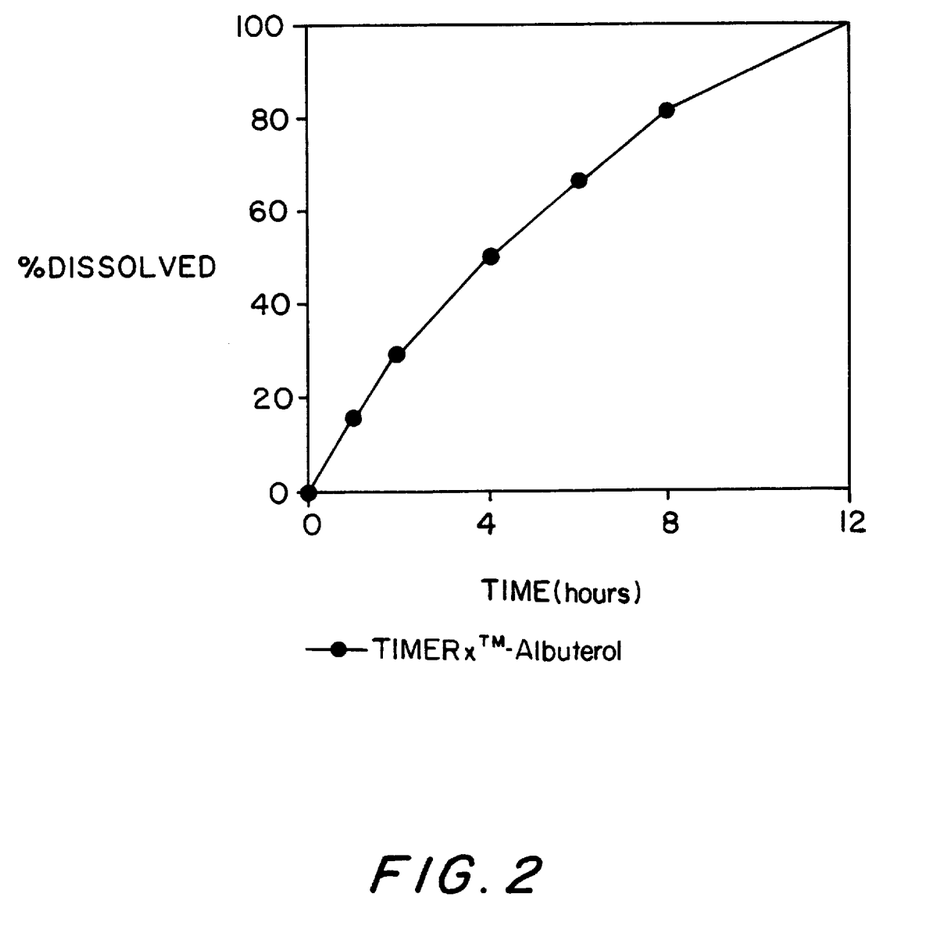
FIG. 2 shows a dissolution profile of an albuterol containing tablet formulated according to Table 14 and Table 15 (Example 10) and conducted as a Type III dissolution with a pH change to simulate gastric passage and stirring at 15 rpm.
Figure 3:
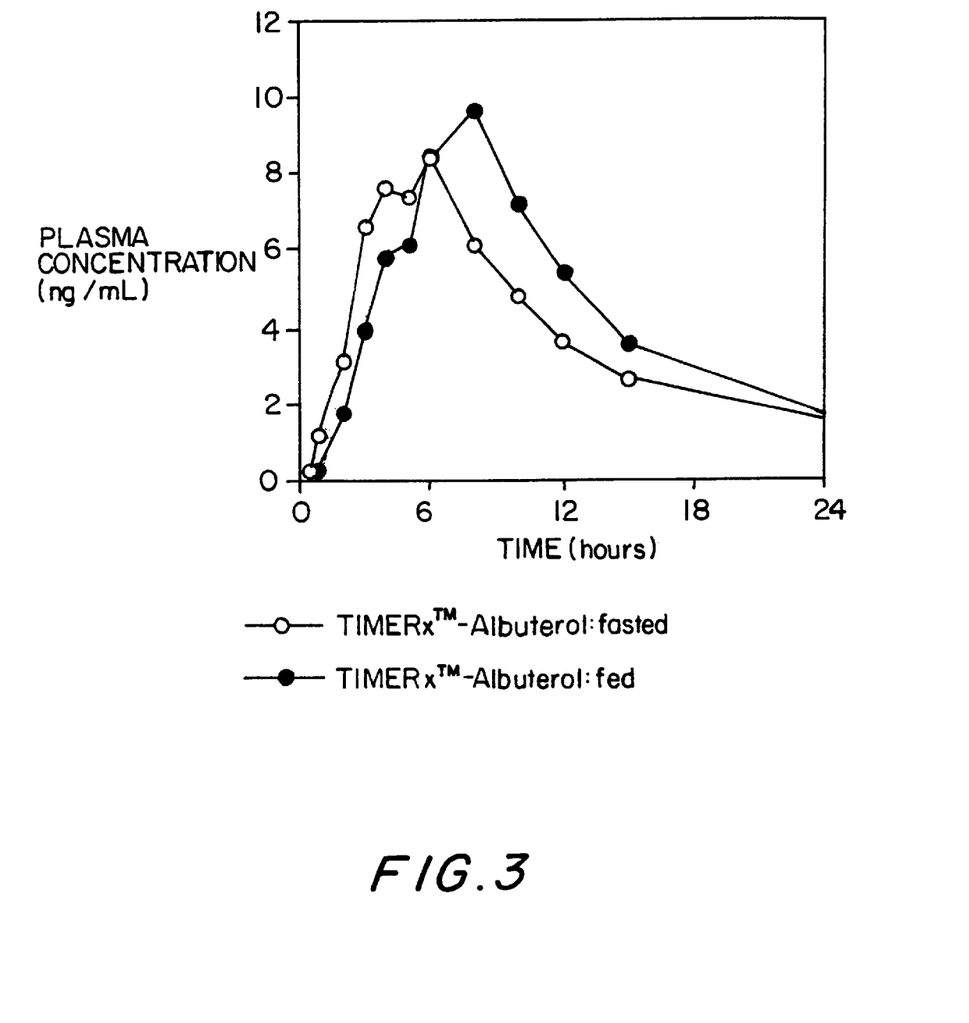
FIG. 3 shows an albuterol plasma profile of provided by ingestion of an albuterol containing tablet formulated according to Table 14 and Table 15 (Example 10): solid circles mark curve of plasma profile in fed subject; open circles mark curve of plasma profile in fasted subject.

FIGS. 1 and 2 show in vitro dissolution profiles for the product formulated according to Table 14 and Table 15 (Example 10) i.e., the formulation of Table 14 with a 2% ethylcellulose coating. The mean in vivo plasma profile for the test product is provided in FIG. 3. FIG. 1 shows a dissolution profile of an albuterol containing tablet formulated according to Table 14 and Table 15 (Example 10) as described above. The dissolution profile of FIG. 1 was conducted as a Type II dissolution with a pH change to simulate gastric and enteric passage and stirring at 50 rpm (acid buffer with a pH of 1.5 for time: 0 though 1 hour followed by alkaline buffer with a pH of 7.5 for time: 1 through 12 hours). FIG. 2 shows a dissolution profile of an albuterol containing tablet formulated formulated according to Table 14 and Table 15 as described above and conducted as a Type III dissolution with a pH change to simulate gastric and enteric passage (pH profile as described by Table 16 above) and stirring at 15 rpm. FIG. 3 shows an albuterol plasma profile of provided by ingestion of an albuterol containing tablet formulated formulated according to Table 14 and Table 15 (Example 10): solid circles mark curve of plasma profile in fed subject; open circles mark curve of plasma profile in fasted subjects.

Analysis of the pharmacokinetic parameters $C_{max}$, $T_{max}$, and $AUC_{28}$ (Table 18) confirms that the tested formulation is an ideal candidate for a 12 hour albuterol formulation. Furthermore, a comparison of the test product in the fed and fasted states show that the test product is not significantly affected by food. A delay of gastric emptying, which is expected in the fed state, accounts for the extended time required to reach the maximum plasma concentration.

TABLE 18

Albuterol Pharmacokinetics

| Parameter | TIMERx fasted | TIMERx fed |
|---|---|---|
| Cmax |  |  |
| mean | 10.5 | 10.6 |
| % CV | 39.0 | 31.0 |
| Tmax |  |  |
| mean | 4.5 | 7.0 |
| % CV | 29.0 | 23.0 |
| AUCInf |  |  |
| mean | 113.4 | 128.1 |
| % CV | 30.0 | 20.0 |

| Ratios | Cmax | Tmax | AUC Inf |
|---|---|---|---|
| TIMERx fasted:TIMERx fed | 0.98 | 0.64 | 0.89 |
| TIMERx fed:TIMERx fasted | 1.02 | 1.57 | 1.13 |

| Confidence Limits | Cmax LL | Cmax UL | AUCInf LL | AUCInf UL |
|---|---|---|---|---|
| TIMERx fed vs TIMERx fasted | 89 | 124 | 102 | 133 |

TABLE 19

| Parameter | TIMERx-fasted | TIMERx-fed |
|---|---|---|
| $AUC_{\infty}$ | 57.3–156.2 | 75.6–161.1 |
| Cmax | 4.6–18.4 | 6.0–15.9 |
| Tmax | 3.0–6.0 | 3.0–8.0 |

| Parameter | TIMERx-fed |
|---|---|
| $AUC_{\infty}$ | 89.9–149.2 |
| Cmax | 7.0–11.9 |
| Tmax | 3.0–10.0 |

Conclusion

From the results provided in above examples, it can be seen that the formulations according to the invention provide a controlled release of an active medicament such as albuterol sulfate without any significant differences induced by a "fed/fast" effect due to the presence of food in the gastrointestinal tract. Accordingly, the results provide that the tablets produced according to the invention are suitable for delivering medicaments as an oral solid dosage form over a 24-hour oral period of time.

The present invention is not to be limited in scope by the specific embodiments described herein. Indeed, various modifications of the invention in addition to those described herein will become apparent to those skilled in the art from the foregoing description. Such modifications are intended to fall within the scope of the claims. Various publications are cited herein, the disclosures of which are incorporated by reference in their entireties.

What is claimed is:

1. A controlled release solid dosage form for oral administration of a therapeutically active medicament to a patient in need thereof, comprising:

a pharmaceutically effective amount of a medicament to be administered to a patient in need of said medicament;

a sustained release excipient comprising a gelling agent; a pharmaceutically acceptable hydrophobic material; and an inert pharmaceutical diluent wherein the ratio of said inert diluent to said gelling agent is from about 1:8 to about 8:1, said dosage form providing a sustained release of said medicament when exposed to an environmental fluid.

2. The controlled release solid dosage form according to claim 1 wherein said inert diluent is selected from the group consisting of pharmaceutically acceptable saccharides, polyhydric alcohols, pre-manufactured direct compression diluents, and mixtures of any of the foregoing.

3. The controlled release solid dosage form according to claim 1, wherein said hydrophobic material is selected from the group consisting of a cellulose ether, a cellulose ester and an alkylcellulose.

4. The controlled release solid dosage form according to claim 1, wherein said hydrophobic material is selected from the group consisting of ethylcellulose, carboxymethylcellulose, cellulose acetate phthalate, hydroxypropylmethylcellulose phthalate and a polyvinyl acetate polymer.

5. The controlled release solid dosage form according claim 1, wherein said hydrophobic material is present in an amount ranging from about 25 percent to about 50 percent, by weight, of the solid dosage form.

6. The controlled release solid dosage form according to claim 1, wherein said medicament is a pharmaceutically effective amount of albuterol or a salt or derivative thereof.

7. The controlled release solid dosage form according to claim 1 which is a tablet.

8. The controlled release solid dosage form according to claim 1, which is in granulate form.

9. The controlled release solid dosage form according to claim 8, wherein said granulate is coated with a hydrophobic material to a weight gain from about 1 percent to about 20 percent.

10. The controlled release solid dosage form according to claim 1, wherein the medicament comprises an amount of albuterol equivalent to about 4 mg to about 16 mg of albuterol free base.

11. A method of preparing a controlled release solid dosage form comprising a medicament for oral administration, the method comprising preparing of a sustained release excipient comprising from about 10 to about 99 percent by weight of a gelling agent, from about 0 to about 89 percent by weight of an inert pharmaceutical diluent, and from about 1 to about 90 percent by weight of a pharmaceutically acceptable hydrophobic material; and adding a therapeutically effective amount of a medicament to said excipient, such that a final product is obtained having a ratio of said medicament to said gelling agent from about 1:3 to about 1:8, wherein said formulation provides therapeutically effective blood levels of said medicament for at least 12 hours.

12. The method of claim 11, further comprising compressing said mixture of said sustained release excipient and said medicament into tablets.

13. The method of claim 11, wherein said medicament is albuterol or a salt or derivative thereof.

14. The method of claim 13, further comprising coating the resultant tablets with a hydrophobic coating to a weight gain from about 1 percent to about 20 percent.

15. A method of treating a patient with albuterol comprising:

preparing a sustained release excipient comprising from about 10 to about 99 percent by weight of a gelling agent from about 0 to about 89 percent by weight of an inert pharmaceutical diluent, and from about 1 to 90 percent by weight of a pharmaceutically acceptable hydrophobic material; and adding an effective amount of albuterol or a salt or derivative thereof to said sustained release excipient, tableting the resultant mixture into tablets such that said tablets have a ratio of albuterol to said gelling agent from about 1:3 to about 1:8, such that a gel matrix is created when said tablet is exposed to gastrointestinal fluid and said tablet provides therapeutically effective blood levels of albuterol for at least 12 hours; and administering said tablet to a patient on a once-a-day or twice-a-day basis.

16. The method of claim 15, further comprising preparing said formulation such that it provides therapeutically effective blood levels of said medicament for at least 24 hours.

* * * * *

UNITED STATES PATENT AND TRADEMARK OFFICE
CERTIFICATE OF CORRECTION

| | |
|---|---|
| PATENT NO. | : 5,958,456 |
| APPLICATION NO. | : 08/886496 |
| DATED | : September 28, 1999 |
| INVENTOR(S) | : Baichwal et al. |

Page 1 of 1

It is certified that error appears in the above-identified patent and that said Letters Patent is hereby corrected as shown below:

On the bibliographic of the patent in line 2 of the text at bracket 63, between "continuation in part of" and "application" insert --application No. 08/447,236, May 22, 1995, U.S. Pat. No. 5,554,387, which is a divisional of--.

In the patent at Col. 1, line 9, between "continuation-in-part of" and "Ser. No." insert --Ser. No. 08/447,236, filed May 22, 1995, now U.S. Pat. No. 5,554,387, which is a divisional of--.

Signed and Sealed this

Fifth Day of February, 2008

JON W. DUDAS
*Director of the United States Patent and Trademark Office*

Disclaimer

5,958,456 — Anand Baichwal, Wappingers Falls, NY (US); Troy W. McCall, New Milford, CT (US). CONTROLLED RELEASE FORMULATION (ALBUTEROL). Patent dated September 28, 1999. Disclaimer filed June 11, 2013, by the assignee, Endo Pharmaceuticals, Inc.

Hereby disclaim complete claims 1-16 of said patent.

*(Official Gazette, July 16, 2013)*

Disclaimer

5,958,456—Anand Baichwal, Wappingers Falls, NY (US); Troy W. McCall, New Milford, CT (US). CONTROLLED RELEASE FORMULATION (ALBUTEROL). Patent dated September 28, 1999. Disclaimer filed June 11, 2013, by the assignee, Endo Pharmaceuticals, Inc.

Hereby disclaim complete claims 1-16 of said patent.

*(Official Gazette, July 30, 2013)*